(12) United States Patent
Rose et al.

(10) Patent No.: US 7,670,818 B1
(45) Date of Patent: Mar. 2, 2010

(54) β-MANNANASE FROM COFFEE BERRY BORER, HYPOTHENEMUS HAMPEI, AND USES THEREOF

(75) Inventors: Jocelyn Rose, Ithaca, NY (US); Ricardo Acuna Zornosa, Chinchina, CO (US)

(73) Assignees: Cornell Research Foundation, Inc., Ithaca, NY (US); Federacion Nacional de Cafeteros de Colombia, Bogota (CO)

(*) Notice: Subject to any disclaimer, the term of this patent is extended or adjusted under 35 U.S.C. 154(b) by 0 days.

(21) Appl. No.: 12/579,499

(22) Filed: Oct. 15, 2009

Related U.S. Application Data

(62) Division of application No. 11/943,015, filed on Nov. 20, 2007.

(60) Provisional application No. 60/866,705, filed on Nov. 21, 2006.

(51) Int. Cl.
    *C12N 5/02* (2006.01)
    *C12N 9/24* (2006.01)
    *C07H 21/04* (2006.01)
    *C12N 15/00* (2006.01)
    *C12N 1/20* (2006.01)
    *C12N 1/00* (2006.01)

(52) U.S. Cl. ............ 435/200; 435/410; 435/252.3; 435/252.33; 435/254.11; 435/320.1; 435/325; 536/23.2; 536/23.1

(58) Field of Classification Search ............ None
    See application file for complete search history.

(56) References Cited

U.S. PATENT DOCUMENTS

| | | | |
|---|---|---|---|
| 5,714,183 | A | 2/1998 | Nicolas et al. |
| 5,795,764 | A | 8/1998 | Christgau et al. |
| 5,854,047 | A | 12/1998 | Buchert et al. |
| 6,566,114 | B1 | 5/2003 | Kauppinen et al. |
| 6,841,662 | B2 | 1/2005 | Marraccini et al. |
| 6,984,406 | B2 | 1/2006 | Cho et al. |
| 7,041,488 | B2 | 5/2006 | Outtrup et al. |

FOREIGN PATENT DOCUMENTS

| | | |
|---|---|---|
| WO | 9506478 A1 | 3/1995 |
| WO | 9720937 A2 | 6/1997 |
| WO | 9806852 A1 | 2/1998 |
| WO | 2004/113538 A1 | 12/2004 |

OTHER PUBLICATIONS

Bewley et al., "Molecular Cloning of a cDNA Encoding a (1-4)-Beta-Mannan Endohydrolase from the Seeds of Germinated Tomato (Lycopersicon esculentum)," PLANTA 203:454-459 (1997).

Broun et al., "Catalytic Plasticity of Fatty Acid Modification Enzymes Underlying Chemical Diversity of Plant Lipids," Science 282:1315-1317 (1998).

Fourgoux-Nicol et al., "Isolation of Rapeseed Genes Expressed Early and Specifically During Development of the Male Gametophyte," Plant Mol. Biol. 40:857-872 (1999).

Giorgini et al., "Effect of Embryo and Exogenous GA3 on Endospermic Endo-Beta-Mannanase Activity of Coffea Arabica L. During Germination and Early Seedling Growth," R. Bras. Fisiol. Veg. 8(1):43-49 (1996).

Joersbo et al., "In Vivo Modification of the Cell Wall Polysaccharide Galactomannan of Guar Transformed with a Alpha-Galactosidase Gene Cloned from Senna," Mol. Breeding 7:211-219 (2001).

Sweetlove et al., "Starch Metabolism in Tubers of Transgenic Potato (Solanum tuberosum) with Increased ADPGlucose Pyrophosphorylase," Biochem. J. 320:493-498 (1996).

Voss, "Perplexing Compounds Rejoin the Club," Science 295:604 (2002).

*Primary Examiner*—Nashaat T Nashed
(74) *Attorney, Agent, or Firm*—Nixon Peabody LLP

(57) ABSTRACT

The present invention relates to an isolated β-mannanase protein having an amino acid sequence which is 90% similar to the amino acid sequence of SEQ ID NO: 1, as well as isolated polynucleotides encoding the β-mannanase protein, and isolated expression systems and host cells containing the polynucleotides. The present invention also relates to a method of recombinantly producing β-mannanase protein. Also disclosed is a method of degrading mannans and polysaccharides in plant material, which involves providing plant material and contacting the plant material with the β-mannanase protein of the present invention under conditions effective to degrade mannans and polysaccharides in the plant material.

9 Claims, 2 Drawing Sheets

β-MANNANASE FROM COFFEE BERRY BORER, HYPOTHENEMUS HAMPEI, AND USES THEREOF

This application is a division of U.S. patent application Ser. No. 11/943,015, filed Nov. 20, 2007, which claims the priority benefit of U.S. Provisional Patent Application Ser. No. 60/866,705, filed Nov. 21, 2006, which are hereby incorporated by reference in their entirety.

FIELD OF THE INVENTION

This invention relates to an isolated β-mannanase protein and uses thereof.

BACKGROUND OF THE INVENTION

Mannanases are enzymes that hydrolyze mannans and related hemicellulosic polysaccharides, such as galactomannan and glucogalactomannan (also termed galactoglucomannan). These polysaccharides are characteristic components of plant cell walls and, so, an important potential commercial use of mannanases is in the degradation of hemicellulosic materials from plant biomass, thus providing a means to recover soluble sugars from these biopolymers. Mannan polysaccharides are also found as storage polymers in the seeds of some plant species, such as those of leguminous plants, and coniferous trees.

In coffee bean, galactomannans accumulate to extremely high concentrations and represent approximately 24% of the dry weight of the bean (Bradbury et al., "Chemical Structures of Green Coffee Bean Polysaccharides," *J. Agric. Food Chem.* 38:389-392 (1990)). These polysaccharides consist of a linear chain of mannosyl residues that are linked to each other via beta 1,4 glycosyl linkages, to which are attached alpha-galactosyl residue monomers. It is known that endo-beta-mannanases (EC 3.2.1.78) hydrolyze mannan polymers during seed germination, thus facilitating the exit of the rootlet during germination and releasing small oligosaccharides which are then used as a source of energy for the growth of the young plant. Indeed, in several plants, it has been shown that endo-β-mannanase activity is mainly detected in the endosperm of seeds undergoing germination (Bewley, "Breaking Down the Walls—A Role for Endo-β-Mannanase In Release from Seed Dormancy?" *Trends Plant Sci.* 2:464-469 (1997)).

Mannanases are produced by microorganisms such as molds, yeasts, and fungi, as well as *Bacillus subtilis, Aeromonas, Enterococcus, Pseudomonas,* and *Streptomyces*. Some higher plants or animals can also produce mannanases; however, no report exists in the literature describing a β-mannanase from insects. Microorganisms that are typically used for commercial production of mannanases include *Trichoderma* or *Aspergillus* spp.

In industrial processes, during the treatment of coffee, mannans and their derivatives constitute a considerable portion of the insoluble sediments. In addition, during the first extraction step in coffee production only approximately 50% of the mannans are soluble and these polymers are therefore responsible for the majority of the secondary precipitations which occur during the subsequent steps. European Patent No. 0676145A demonstrated that it is possible to hydrolyse coffee galactomannans using an immobilized mannanase extracted from *Aspergillus niger*.

The present invention is directed to overcoming these and other limitations in the art.

SUMMARY OF THE INVENTION

One aspect of the present invention is directed to an isolated β-mannanase protein having an amino acid sequence which is 90% similar to the amino acid sequence of SEQ ID NO: 1. The present invention also relates to an isolated polynucleotide encoding the β-mannanase protein, and an isolated expression system and host cell containing the polynucleotide.

Another aspect of the present invention is directed to a method of recombinantly producing β-mannanase protein. This method involves providing a host cell containing the polynucleotide of the present invention and culturing the host cell under conditions effective for the host cell to express β-mannanase protein. The β-mannanase protein is recovered.

A further aspect of the present invention is directed to a method of degrading mannans and polysaccharides in plant material. This method involves providing plant material and contacting the plant material with the β-mannanase protein of the present invention under conditions effective to degrade mannans and polysaccharides in the plant material.

The present invention relates to an isolated polynucleotide sequence which encodes a mannanase enzyme involved in the hydrolysis of mannan polysaccharides, including unbranched or branched mannan molecules linked to each other via a beta 1,4 glycosyl linkage. The polynucleotide is isolated from an insect (coffee berry borer, *Hypothenemus hampei*) genome.

DETAILED DESCRIPTION OF THE INVENTION

Figure 1:
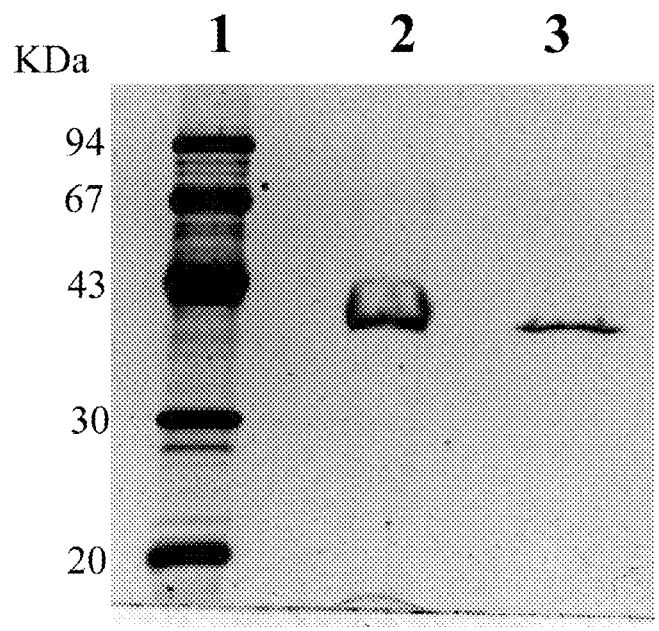
FIG. 1 is a photograph showing SDS-PAGE analysis of the recombinant β-mannanase protein according to one embodiment of the present invention expressed in recombinant baculovirus. Lane 1: molecular mass markers (kDa); Lane 2: Speed-vac concentrated protein; Lane 3: 6×-His tagged mannanase purified using paramagnetic particles.

One aspect of the present invention relates to an isolated β-mannanase protein from coffee berry borer (*Hypothenemus hampei*) having an amino acid sequence of SEQ ID NO: 1, as follows:

```
Met Thr Ala Asp Thr Leu Thr Arg Ala Leu Leu Leu Leu Leu Leu Leu
1               5                   10                  15

Arg Ala Ala Ala Ala Val Pro Gly Phe Thr Val Ser Gly Thr Arg Ile
            20                  25                  30
```

-continued

```
Leu Asp Ala Asn Gly Gln Glu Phe Met Ile Arg Gly Val Ser His Ala
         35                  40                  45
His Thr Trp Tyr Lys Asp Ile Asn Gly Ala Ile Thr Ser Ile Ala
 50                  55                  60
Ala Ala Gly Ala Asn Thr Val Arg Ile Val Leu Ser Asn Gly Gly Gln
 65                  70                  75                  80
Trp Thr Lys Asp Asn Leu Asp Ser Val Gln Asn Ile Leu Ser Leu Cys
             85                  90                  95
Glu Ser His Lys Leu Ile Ala Met Leu Glu Val His Asp Ala Thr Gly
            100                 105                 110
Asn Asp Ser Gln Glu Thr Leu Glu Asn Ala Val Asn Tyr Trp Lys Glu
            115                 120                 125
Leu Arg Asp Leu Leu Ile Gly Lys Glu Asp Arg Val Ile Ile Asn Ile
130                 135                 140
Ala Asn Glu Trp Phe Gly Thr Trp Asp Thr Ala Gly Trp Ala Asp Gly
145                 150                 155                 160
Tyr Lys Val Val Ile Pro Glu Leu Arg Asn Ala Gly Leu Glu His Leu
                165                 170                 175
Leu Val Val Asp Thr Ala Gly Tyr Gly Gln Tyr Pro Gln Ala Ile Phe
            180                 185                 190
Glu Lys Gly Lys Glu Val Phe Gln Thr Asp Leu Leu Ala Arg Thr Val
            195                 200                 205
Phe Ser Ile His Met Tyr Glu Tyr Ala Ala Thr Asp Val Thr Met Ile
            210                 215                 220
Lys Gly Asn Ile Asp Ser Ala Leu Asn Thr Gly Ile Pro Val Ile Ile
225                 230                 235                 240
Gly Glu Phe Gly Asp Arg Lys Pro Glu Ser Gln His Val Asp Ile Asp
                245                 250                 255
Thr Ile Met Ser Tyr Thr Arg Glu Lys Ser Val Gly Trp Leu Ala Trp
                260                 265                 270
Ser Trp Tyr Gly Asn Gly Asn Asp Glu Ser Ile Leu Asp Leu Thr Asn
            275                 280                 285
Gly Pro Ser Gly Asp Tyr Ser Leu Thr Asn Val Gly Ser Gln Ile Val
            290                 295                 300
Asp Ser Glu Asn Gly Ile Arg Lys Thr Ser Thr Ile Cys Ser Ile Phe
305                 310                 315                 320
Asn
```

The present invention is also directed to isolated β-mannanase proteins having an amino acid sequence which is at least 90% similar, at least 91% similar, at least 92% similar, at least 93% similar, at least 94% similar, at least 95% similar, at least 96% similar, at least 97% similar, at least 98% similar, and/or at least 99% similar to the amino acid sequence of SEQ ID NO: 1.

The polynucleotide encoding the β-mannanase protein of SEQ ID NO:1 has a sequence of SEQ ID NO:2, as follows:

```
gctgatcggg tgtgtactca attctttaag gagtttacaa tatgaccgct gatacattaa    60
cgcgggcact gctgctgttg ctgttgttgc gcgctgctgc tgctgtaccc ggattcacgg   120
tttccggtac tcgaatttta gatgctaacg gtcaggaatt tatgataaga ggggtcagtc   180
acgcacatac ctggtataag gatgatatta atggggccat cacatccatc gctgctgctg   240
gcgccaacac ggttcgcatt gtactttcta atggcggaca gtggacaaaa gacaacctgg   300
attcagttca gaacattctg tccctctgtg agagccataa gcttattgcc atgctggaag   360
ttcacgatgc caccggcaat gacagccaag aaacactgga aaatgccgtg aattactgga   420
```

-continued

```
aagagcttcg ggacttgctc attggtaagg aagacagagt tattatcaat atagccaatg    480
agtggttcgg tacctgggat actgctggct gggccgacgg ttataaagtt gtcattccgg    540
aactacgtaa cgccggactg gaacacctgc tggttgtaga cacagcggga tacggacaat    600
atcctcaagc tattttgaa aaaggtaagg aggttttcca gacagacctt cttgcccgca    660
cggtgttttc cattcacatg tatgaatatg cagcgacgga tgtaacaatg ataaaaggaa    720
atattgactc ggccttgaat acaggcatcc cggtgattat tggagaattt ggtgaccgaa    780
aaccggagtc gcagcatgtt gatatcgata ccatcatgag ctacactcgc gagaaatccg    840
taggctggtt ggcctggtcc tggtacggta acggtaacga tgaatcaatt cttgacctga    900
cgaacggacc tagcggagat tacagtctta ctaacgtggg gagtcaaatt gttgacagtg    960
agaacggcat tcgcaaaacc tccacaatct gttcaatatt caattaaaaa aaaagatgtt   1020
tgtttgtgca tttttgttat aataaacgtt tcatttgcat att                     1063
```

Isolated polynucleotides having at least 90% similarity, at least 91% similarity, at least 92% similarity, at least 93% similarity, at least 94% similarity, at least 95% similarity, at least 96% similarity, at least 97% similarity, at least 98% similarity, and/or at least 99% similarity to SEQ ID NO:2 are also encompassed by the present invention.

The genomic sequence from which the isolated polynucleotide of SEQ ID NO:2 is derived has a sequence of SEQ ID NO:3, as follows:

```
atggttgagt tcaccaatca agaatatgca gacatgcatt tgatttatgg ccaagccaat     60
ggcaattcct acgaagcgcg cagactctac gcacgtagat atcctaatcg gagactacct    120
gatccaaaaa catttccaaa tattcacatt cgactatgtg aaactggaac atataaacag    180
ttcagtggtt tcgaaggagt acatcaaatc gcgagaactc cagaaatcga agaagccgtt    240
ctaaatagtg ttgaagccga tcctgctacg agcacaagga aaattgcaat aacattgaac    300
atttcattta tgcttgtctg aagaattctg actgataacc ttttgtatcc ttaccaccttt    360 acaagggttc aagctcttct cccacgagac tttcctttag gcgtaaattt ttgcgagtag    420
ttcttacaaa tgctggctca aaatccgtcg tttgcatcgt ttgcgtcgtt ttgttttattt    480 tatttacgga tgaagcaaat ttttcaagaa attccatccg aaatttttcat aatgaacatt    540 tttggggaga agaaaatcca catttagtac gagaaaacaa ttttcaacat caattttctg    600
tcaacgtttg ggcaggaatt attggcgatt atttaatagg accatttttt ctgtcgaaga    660
ggttgaatgg tggctattat catcggtttt tcgaagagga acttcccgta cttttagatg    720
aggtaccgct tcttttgaga aaccaaatgt ggctaatgca cgatggtgcg ccagtccatt    780
ttagtcggga agtaagggag ttcctaaatg aacattatca caaccgttgg attgatcgag    840
ggggaactca gtcatggccc ccgaggtccc cggacctgaa tagtctggat ttttttttct    900
agggacatct caaatccttg gtgtaccaaa ccccaattaa cacagtggag gaattgcgaa    960
acagaatagt cgattcatgt aacgtcattc gcaatactcc tggtattttt gaaagagtcc   1020
gccggtctat gaggcacaga gcggaatctt gcatcttagc aagaggagga catttcaac    1080 agttcctata gtcttgtttt atttagatta aattactttt actgttacct tacgaattta   1140
atacataaga ttcattgtac tcttttgttg tacgttttcc ttaatatgca tcggtaactg   1200
tttatgcaaa tttttcgcaa atgataaaag atacgagaaa aatgcaagag atcaaaaagt   1260
aagagaaata gacaaggaat ctaaatgtga aatcaaaatt tatacatagt gttccaaaaa   1320
aaagttagga agcaaaaaat agcacatgac ccaagaaaac ataagaccct gtatatggag   1380
agcaacgatt ttgccatttt catatagagg ctcttaaaaa atatagatat accaaatttc   1440
```

-continued

```
attaaattat ctttaggcat aagaaagaaa atagtagaaa atttaaaaaa aatcaaactt    1500
tatcaccctg tatatcaaaa atggtgcgtt tttccccata ggtgtattag catttttttc    1560
ttattttgcc gaatactatc accccctgaa atatctccat gatgatctgt tacaccctgt    1620
acacctaaaa agtaaaataa taaaacgttt aaatttatc ttttaacgta gataagattt     1680
tgcgtccttt gtttccttct aagttttaat cgagatttcg cctcattttc gctcattcgc    1740
cagaagacct cagtgaaagc gattcattaa gtctgaaatt taactttgtt ccctaccgaa    1800
tattcttttt ctgacgatag acgatagctg atcgggtgtg tactcaattc tttaaggagt    1860
ttacaatatg accgctgata cattaacgcg ggcactgctg ctgttgctgt tgttgcgcgc    1920
tgctgctgct gtaccggat tcacggtttc cggtactcga attttagatg ctaacggtca     1980
ggaatttatg ataagagggg tcagtcacgc atacctgg tataaggatg atattaatgg      2040
ggccatcaca tccatcgctg ctgctggcgc caacacggtt cgcattgtac tttctaatgg    2100
cggacagtgg acaaaagaca acctggattc agttcagaac attctgtccc tctgtgagag    2160
ccataagctt attgccatgc tggaagttca cgatgccacc ggcaatgaca gccagaaaac    2220
actggaaaat gccgtgaatt actggaagaa gcttcgggac ttgctcattg gtaaggaaga    2280
cagagttatt atcaatatag ccaatgagtg gttcggtacc tgggatactg ctggctgggc    2340
cgacggttat aaagttgtca ttccggaact acgtaacgcc ggactggaac acctgctggt    2400
tgtagacaca gcgggatacg gacaatatcc tcaagctatt tttgaaaaag gtaaggaggt    2460
tttccagaca gaccttcttg cccgcacggt gttttccatt cacatgtatg aatatgcagc    2520
gacggatgta acaatgataa aaggaaatat tgactcggcc ttgaatacag gcatcccggt    2580
gattattgga gaatttggtg accgaaaacc ggagtcgcag catgttgata tcgataccat    2640
catgagctac actcgcgaga atccgtagg ctggttggcc tggtcctggt acggtaacgg     2700
taacgatgaa tcaattcttg acctgacgaa cggacctagc ggagattaca gtcttactaa    2760
cgtggggagt caaattgttg acagtgagaa cggcattcgc aaaacctcca caatctgttc    2820
aatattcaat taaaaaaaaa gatgtttgtt tgtgcatttt tgttataata acgtttcat     2880 ttgcatatta aatatactaa tccaatatat atttatagac aatagattat taaaaagta     2940 aattttaaaa taacttcttc aaaaaagaac atttacgctc aaagtgacct atagacgtca    3000
ataatttaaa atgtcactct tcgcacattg acaataacct gcatagacgt ctatgaacgt    3060
cgttgtctat agacgtgttc ctttaattgt tttctaaagc tttgatcaat tggttcagaa    3120
aaacggttca atagattcat ttaataattt acaggactat tgggggtaca ttaggctata   3180
aaacggcctc tcaatatttg tcttcccatc aatatttaaa aagtaatagt agatttgtta    3240
aaggactgta aaatgtaatt ttttagtagt ttttccaaat taaagctaag agtaaaaaaa    3300 acggttttc tacaaaagtc atggaagggt tttgtaggga atttaatcag gttttaaaa      3360 ctatccttga aattaaagtt tacttaagcg atcactggtt gctgagatat cgatgatcaa    3420
agataaaagg atccttttc tttcaaagtt agatgtctca gcaagggatt gacgtagatg     3480
tatgaaaaaa aaaacaaaat gaagctgaat aaacaaggta accgaccact gtacgacaag    3540
ggttcaaatg gaaaaaatt tctgagaccc atggagactt agaagaaga agaaaatttt      3600 gaaaaatgtt tacctcgcgc catttcttgg gattgcgcgg taaccataac tccaaggaa     3660 attccgatgt aagatctgaa aactataaaa cattaagctt caaatgctt ttttctccaa     3720 ctcgatacga ccgttttttc acaaagatac tcaaagaaca ctaaaaaaaa taaaaaaagg    3780 ttttacttt aattttttgg attagtatta ttaacattat ttaatctaaa ataatactga     3840
```

-continued

```
tattggtatt aactttcacc aggtacactg gtttcaatag aaacgttacc aatttagtta    3900
catagcatca aagaaaagaa tgacattatg atcatcaatt ataattgatt gttcgattat    3960
aatataacta ttattgatta ttatattatt ataattctct taggtattaa gcccttaagt    4020
caaaaatcgt agttttctac aaaacgagat taaaaatttt ataacgctat gcaacagaaa    4080
aaaaaattca ctgggtttac agtacgtggt gatgatacct cactatttac tcaattaata    4140
tttatatata aaatagtccc atcaattatt taaattttca aaaaaaaaat ttattaaatt    4200
gttcaacaaa gagttaacaa taatttcaca atagttaaga actaatttct taattttcaa    4260 tatgccccc ttcctgtaaa atacacttat ctattcgttt tctgatgtgt tgcacaactt     4320
aaataataaa tgttgtaata tttcttgaaa atttaattaa ggttaccaga tgtcactttt    4380
ttacaattat tctaacaaga gttgagtgat agtttagggt tcgatccctg ctacctccga    4440
tatttttttt tttcgttttt tttttgttaa taacaatagt aataattgtc aaaataatta    4500
aaaacgataa aaataattta tttgacgcat tttacagtta tttaaagctt gtaatgagag    4560
aatttatatg attcgcatat taaattaagg attttcacta caaatttcat atttcaaaaa    4620
caattggtcc tattttaata aaattatcta ccaggaggtt tttgatgatg ctctttcata    4680
atatgttaaa aaaatgcgtt taaaattacc ctaatacatt tttctgtaaa atctacccta    4740
atatttaact ataaaaacgt acgccaatga cgaagggaaa ccattttagg caaatcacaa    4800
tcggaattca aagatacaca actgatccaa atttgaagtg aatcggctaa acagtttttg    4860
agatacaaaa gtggctccat gaatcgtgcg acatactata tgcgatcaaa ataagacttt    4920
tttttcctat aaacatgtgc cctaaaatgc accccctcca aactcagcc attctaagtt     4980 gcgcgacaaa aatcaattat tttaaatttt gactacagtt atggatcaaa tttttgaaaa    5040
attgcacatc cgttttctt aaacactgta ttcatttctt gctttaaaaa taacgtaacc     5100
ctaattttag agaagatgga gagggatcca cttattgcgt aaataaaatt taatgtttcc    5160
aacgagaaat cctaacttta accatcagca tctagtagac catggaaaaa tctaaaattt    5220
atctctagca ttttcttaat gcaactaatc gaatctttac aggacctgac ataaaaaaat    5280
taattgatga tacctctttt ttatcaagtc tcatttacat agaataacag gcatgattag    5340
catttgttga cgtcacaaaa aattttctcg gcaattacaa atcaacagat ttctgtgaaa    5400
aaattaattt aatgttgaat gcctatcaga aattagggtg caatatatca ctgaaaattc    5460
atttcttgca atatcactta agttttttcc gaaaaatatg gattcagtta gtaatgaact    5520
aggtatatgt gcggtaaatt tatgttgcaa aaaaatgtac gcagattacc tgaattataa    5580
caacaaagtt gtcgaaaaat gtcgaaacac ctccgaaaat tgaaacatag caaaaattat    5640
ccgagtcatt tatgcacttg aattcgtgat ttcttttact catttcacaa atttattaca    5700
tgattaaaat taaattattt attaaattac aagagaatga taaaaaaaat aattaaggct    5760
tttaaatgtt gtatatgaac tgtcacaccg taacagattt gtcaacatat taacaattga    5820
cagtaaaaat ttcaaattta taattcggtc atccattaga aaattcataa cttcactatt    5880
tatccataaa tttgcatcca aagtaacttg ttcttttcat gaatgtgtca gctctacata    5940
aaacaattga aactggacct atctttgcga tttctatttt ttccagggcc atatgggaaa    6000
ctttgcaata aatcttgtgc aataaattat gacaattagg aatatttggt gcggtgtaca    6060
tattatatac aggttgaaga aaataccctcc cccataaaag ggccttcaaa atagtctaat    6120
acaattttgc ccttaaacga acagggaaga taatattaaa ggatattgaa atttatatgg    6180
gttttcctat tgtcggtccg gaggggcaac atccaatata ctatatgaaa taaagttgtc    6240
```

-continued

```
tatagttagt acattgttaa taatttgatt ttcatatatt ctgtattcag tttctaccgt  6300
acaagtagcg gcggagatgt ggatgtcatg tattattaaa cttgtatgga aaaaaaggat  6360
aaaaaaggac acttatatct ccaccattga tgaatggtta aagctggtaa tttttttggaa  6420
```
(Note: the line ending "6420" reads "aaaaaaggac acttatatct ccaccattga tgaatggtta aagctggtaa ttttttggaa")

```
tacacctacc gatatgctaa actcatatac gaaatttggt taaaaaatct taagccgttt  6480
tggaatttaa aaaataaaga aatgttcttt tttttaaact ttaacacccct gtatctcgga  6540 aacggtgcgt ttgcgggccc atgttcatat aaacttttt gcttattttt gtctgaagaa  6600
tcatcccttg aaatttatgc acgtacttaa ttaacacccct gtatttcacg taccatgtcc  6660
tactatacct aaactcaaca gttggcgaga aattttgttg tcgtacctgg tttttgggcc  6720
atcctgtata catggattta tcatcacaaa acctcaacc aaaaataaaa attgacgtgt  6780
atgagcgttt ttttttttg aaaaacaaat ttctgaattt taaatgaatg tattccttat  6840
tttatcataa acctgtatat aaatttaaaa aaaacgtgat gtgatacgtg aaaactaagt  6900
tgttatttgg attcagcagg acaaaattta tatgttttat ctaaaattat gcaaaaaata  6960
ttttcatcgc agacccgtgt tatcaatgta aaaattaatt aaacccctcc gtaaaagcca  7020
gcgttttgac atttgaatgt ttccgcccca atgttgaagg gaaaaataaa aagttactag  7080
aatgtaacta gttaggctgc catatttgga gtaacatgtt ccctctctct ctctaacaca  7140
cgtgaacata actttgcggt actgtataga tttagtgact gtacctacat agtcatacgt  7200
atggaaactt atacagtgta tcaatttaaa aactagcaat ggagaatatc ttctaaatga  7260
aaagtgctat caggacgatc tcaaaaacgt atcgggggat tcgaaaagga accaaaatga  7320
tatattaatc aatccgtttt cacttatccc ctcgccccca accaccccaa cgttcagaat  7380
ttcaaatggc accatctgtc atgtaatacc tcaaatggaa ggtatttcaa aactgcattt  7440
aggggtataa ttagatttta atttattgat tcgttttttga gaaaaagtgc ctcaaaaagg  7500
taaaattaaa aatttttaata ttgtttctta caaaacaat taggttttca atacatgttg  7560
ttaggaacag ggccggattt agggcagggc aggcggggct actgccccgg ggcctccaca  7620
aggaaggggc ccccacaata gagaaaaata aatatcgaaa tttcgacggg tcagcaactt  7680
ttaatttttt ttagttttttt caatacttaa gtgtcttttcg ggacccgtgg agcgaattgg  7740
ggtgctgggt ggggtaaaca actagctccg agtgtgctaa ttgcggcgtt ctttaaaaaa  7800
aataatttat ttttgtttct tttttttcatt ttctggcgtt tcctggatgc caaaaatatg  7860 tttttttttct caaaactgta aatgtcgtta aagcgttacg daccccaagt ttccatttac  7920
tgtcaatttt ttatttttatc aagcatctcg gtggcaatac ttttttttta atgtgtaatt  7980
tgtaatttgt gctcatgagt taaaagaaa taaaataagt aaaagaaat tccaaggttt  8040 tataaaagt atatatggta accgggtgac tattaaaatt tcttctcaag taggctttgg  8100
aattatttga caccgagtcc gtatgtctta gatttattaa cagattcgta tttaagtgag  8160
gttgggttta tttgtttata ttcgaaacta agtaaagaac atatcaaaga cttacggact  8220
cgctgtcaaa taattccaca gcctacttga gaagaaattt taatagtcac ccgttataaa  8280
tacgatttaa atcttacggt tggcaacact gtcgtggtta agaagtgtcc gagtgtagcg  8340
tgctcgaagc ggggaatccc taaattttat tagaagctac ggacgtattg caacaaaagt  8400
aaaatcttct gaatttatat ctacaaacac acgtaagtat tttcgtattt atcttgtgat  8460
ctataagata taatgaattt tatatttcat tgtgcaatta cgaaaatttg ttttttttc  8520 ttaaaggagc gatatgcttt aaagagcaaa acgtaaaaca gaggttatgg aggttttatt  8580
ccacgactac attcttattt tcttaagatt tcttttacaa tggtattatg agtgatcgcc  8640
```

```
-continued
ataaaactcc tcgagttttc gctagtggat cccaaaaaag gaaattgcaa acagaacgtg  8700
aaaaaaaaaa agtgaagaaa atttagctaa aatacccaaa ttgaccaact attttacatc  8760
gacacccaaa caaaaacttc cgcaagatcc tgaaaaatca gcagaagatt cagcagtaga  8820
tggagatggg gttgatagta atcaagataa tccagctgtt acatcaggcg acaccatagg  8880
atcttcaaaa acttgtagtc acaatcaaga ggaagtagat tttcgtggtt tcaaaaatga  8940
cattggtctt tggcctgacg tcataacaga agaaatgatc aaatattggg cgaagaaggg  9000
ttccacaaaa ctgcaaaact gtgatgaagt ttctctgcag aattcagttc tccaagacca  9060
gtcgcaagat aataaaaact ttgttcggaa atgttcaaag aatatgttta cacgtcgcaa  9120
tcaaaatcaa gagactgtta atcgattctg gctttgtttt tctccaacta agggaaaagt  9180
atattgctat gcatgtaaat taatgtccac tcaaaaacga agctaagtgg ggaaggcttc  9240
agtgactgga aacatgcatc tgagcggctg tacgagcatg agatttcaaa aactcatttg  9300
gaatcagtga tgaatttagt gcaacgagga gaagtcacag gacgtatcga tcaagagtta  9360
acgatacaag aggcacaaca aattgaatat tggcgaaaaa ttcttacaat tgtcgtcagt  9420
acgattaaat tcattgctga acgcggatta gcctttcgag gagacgatga aattattgga  9480
tcatcgagaa atggcaattt tctgggtatt ttagaattgc tagccgagta cgaaccaatc  9540
ttggcagctc atttaaaaca gcatgcaaac aaagggagag gtcacgtcaa ttatctttct  9600
tctacgatct gcgaagaact gacaaattcc atgggtgatc aagtgttcaa tgaaatcgta  9660
gcaaggatta aaaaatcaaa gtactattct gtttcagtgg actctactcc tgacgaatct  9720
catatcgatc aacttactat agttattcgc tatattgaag gatcgatgcc aaaggaacga  9780
tttcttattt tttaccaaat tgcggtcata ctggtgaagc cacagcaaaa gctttactac  9840
aatttttaag ttaccatcaa attgacatcc ttaattgccg aggtcaatcg tacgacaatg  9900
ctgcaaatat gagtggtaaa tatcaaggga tgcaagctct tattttgcag aaaaatcatt  9960
tatctacgtt tgtaccatgt tgtggtcact cactcaactt agttggaaag gcagctgcta 10020
actcttgtgc atcggcagtt caattctttg atttcgttca gaatttatat acgttttta  10080 cagcaagtac acaacgatac cgaattctgt ctgaaaaatt atcagagaaa aaaagcggac 10140
agtcatatgt tttaaaaaat cttagcgata ctcgctggtc atgtagggtt gcagccacga 10200
aggccattgt tatgggatat tctgaaatcg aagaagctct aaccagcata tcttctgata 10260
aggaacagaa agat                                                  10274
```

The determination of percent identity, i.e. sequence similarity, between two amino acid sequences or two nucleotide sequences can be accomplished using a mathematical algorithm. A preferred, non-limiting example of a mathematical algorithm utilized for the comparison of two sequences is the algorithm of Karlin et al., "Methods for Assessing the Statistical Significance of Molecular Sequence Features by Using General Scoring Schemes," *Proc. Natl. Acad. Sci.* 87:2264-2268 (1990), which is hereby incorporated by reference in its entirety, modified as in Karlin et al., "Applications and Statistics for Multiple High-Scoring Segments in Molecular Sequences," *Proc. Natl. Acad. Sci.* 90:5873-5877 (1993), which is hereby incorporated by reference in its entirety. Another non-limiting example of a mathematical algorithm utilized for the comparison of sequences is the algorithm of Myers et al., CABIOS (1989). Such an algorithm can be incorporated into the ALIGN program (version 2.0) which is part of the CGC sequence alignment software package. Additional algorithms for sequence analysis are known in the art and include ADVANCE and ADAM as described in Torellis et al. "ADVANCE and ADAM: Two Algorithms for the Analysis of Global Similarity between Homologous Informational Sequences," *Comput. Appl. Biosci.* 10:3-5 (1994), which is hereby incorporated by reference in its entirety, and FASTA described in Pearson et al., "Improved Tools for Biological Sequence Comparison," *Proc. Natl. Acad. Sci.* 85:2444-8 (1988), which is hereby incorporated by reference in its entirety.

The isolated β-mannanase protein of the present invention is preferably produced in purified form by conventional techniques. For example, to isolate the protein, a protocol involving a host cell such as *Escherchia coli* may be used, in which the *E. coli* host cell carrying a recombinant plasmid is propagated, homogenized, and the homogenate is centrifuged to remove bacterial debris. The supernatant is then subjected to sequential ammonium sulfate precipitation. The fraction containing the β-mannanase protein can be subjected to gel filtration in an appropriately sized dextran or polyacrylamide column to separate the protein or polypeptide. If necessary, the protein fraction may be further purified by HPLC. Isolated β-mannanase proteins of the present invention may also be produced according to a protocol involving insect host cells, preferably Sf9 insect cell lines.

The present invention is also directed to fragments of the β-mannanase protein of the present invention. Fragments of the β-mannanase protein can be produced by digestion of a full-length protein with proteolytic enzymes like chymotrypsin or *Staphylococcus* proteinase A, or trypsin. Different proteolytic enzymes are likely to cleave the β-mannanase protein at different sites based on the amino acid sequence of the protein.

In another approach, based on knowledge of the primary structure of the protein, fragments of the genes encoding the protein may be synthesized by using a PCR technique together with specific sets of primers chosen to represent particular portions of the protein of interest. These then would be cloned into an appropriate vector for expression of a truncated peptide or protein.

Chemical synthesis can also be used to make suitable fragments. Such a synthesis is carried out using known amino acid sequences for the protein being produced. Alternatively, subjecting a full length β-mannanase protein of the present invention to high temperatures and pressures will produce fragments. These fragments can then be separated by conventional procedures (e.g., chromatography, SDS-PAGE).

Variants may also (or alternatively) be made, for example, by the deletion or addition of amino acids that have minimal influence on the properties, secondary structure and hydropathic nature of the protein. For example, a protein may be conjugated to a signal (or leader) sequence at the N-terminal end of the protein which co-translationally or post-translationally directs transfer of the protein. The protein may also be conjugated to a linker or other sequence for ease of synthesis, purification, or identification of the protein.

The protein of the present invention is preferably produced in purified form (preferably at least about 80%, more preferably 90%, pure) by conventional techniques. Typically, the protein of the present invention is secreted into the growth medium of *Helicobacter* cells or host cells which express a functional type III secretion system capable of secreting the protein of the present invention. Alternatively, the protein of the present invention is produced but not secreted into growth medium of recombinant host cells (e.g., *Escherichia coli*). In such cases, to isolate the protein, the host cell (e.g., *E. coli*) carrying a recombinant plasmid may be propagated, lysed by sonication, heat, differential pressure, or chemical treatment, and the homogenate is centrifuged to remove bacterial debris. The supernatant is then subjected to sequential ammonium sulfate precipitation. The fraction containing the polypeptide or protein of the present invention is subjected to gel filtration in an appropriately sized dextran or polyacrylamide column to separate the proteins. If necessary, the protein fraction may be further purified by HPLC.

The present invention also relates to an isolated polynucleotide encoding the β-mannanase protein, and an isolated expression system and host cell containing the polynucleotide.

Another aspect of the present invention is directed to a method of recombinantly producing β-mannanase protein. This method involves providing a host cell containing the polynucleotide of the present invention and culturing the host cell under conditions effective for the host cell to express β-mannanase protein. The β-mannanase protein is recovered.

The polynucleotide of the present invention may be inserted into any of the many available expression vectors using reagents that are well known in the art. In preparing a DNA vector for expression, the DNA sequence may normally be inserted or substituted into a bacterial plasmid. Any convenient plasmid may be employed, which will be characterized by having a bacterial replication system, a marker which allows for selection in a bacterium, and generally one or more unique, conveniently located restriction sites. Numerous plasmids, referred to as transformation vectors, are available for plant transformation. The selection of a vector will depend on the preferred transformation technique and target species for transformation. A variety of vectors are available for stable transformation using *Agrobacterium tumefaciens*, a soilborne bacterium that causes crown gall. Crown gall is characterized by tumors or galls that develop on the lower stem and main roots of the infected plant. These tumors are due to the transfer and incorporation of part of the bacterium plasmid DNA into the plant chromosomal DNA. This transfer DNA (T-DNA) is expressed along with the normal genes of the plant cell. The plasmid DNA, pTi, or Ti-DNA, for "tumor inducing plasmid," contains the vir genes necessary for movement of the T-DNA into the plant. The T-DNA carries genes that encode proteins involved in the biosynthesis of plant regulatory factors, and bacterial nutrients (opines). The T-DNA is delimited by two 25 bp imperfect direct repeat sequences called the "border sequences." By removing the oncogene and opine genes, and replacing them with a gene of interest, it is possible to transfer foreign DNA into the plant without the formation of tumors or the multiplication of *Agrobacterium tumefaciens* (Fraley et al., "Expression of Bacterial Genes in Plant Cells," *Proc. Nat'l Acad. Sci.* 80:4803-4807 (1983), which is hereby incorporated by reference in its entirety).

Further improvement of this technique led to the development of the binary vector system (Bevan, "Binary *Agrobacterium* Vectors for Plant Transformation," *Nucleic Acids Res.* 12:8711-8721 (1984), which is hereby incorporated by reference in its entirety). In this system, all the T-DNA sequences (including the borders) are removed from the pTi, and a second vector containing T-DNA is introduced into *Agrobacterium tumefaciens*. This second vector has the advantage of being replicable in *E. coli* as well as *A. tumefaciens*, and contains a multiclonal site that facilitates the cloning of a transgene. An example of a commonly used vector is pBin19 (Frisch et al., "Complete Sequence of the Binary Vector Bin19," *Plant Molec. Biol.* 27:405-409 (1995), which is hereby incorporated by reference in its entirety). Any appropriate vectors now known or later described for genetic transformation are suitable for use with the present invention.

Suitable vectors for practicing the present invention may also include, but are not limited to, the following viral vectors such as lambda vector system gt11, gtWES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993), which is hereby incorporated by reference in its entirety), pQE, pIH821, pGEX, pET series (Studier et al, "*Use of T7 RNA Polymerase to Direct Expression of Cloned Genes,*" Methods in Enzymology 185:60-89 (1990), which is hereby incorporated by reference in its entirety), and any derivatives thereof.

U.S. Pat. No. 4,237,224 issued to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

A variety of host-vector systems may be utilized to express the protein-encoding sequence(s) of the present invention. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

The protein according to the present invention can be incorporated into an appropriate vector in the sense direction, such that the open reading frame is properly oriented for the expression of the encoded protein under control of a promoter of choice. This involves the inclusion of the appropriate regulatory elements into the DNA-vector construct. These include non-translated regions of the vector, useful promoters, and 5' and 3' untranslated regions which interact with host cellular proteins to carry out transcription and translation. Such elements may vary in their strength and specificity. Depending on the vector system and host utilized, any number of suitable transcription and translation elements, including constitutive and inducible promoters, may be used.

A constitutive promoter is a promoter that directs expression of a gene throughout the development and life of an organism. Examples of some constitutive promoters that are widely used for inducing expression of transgenes include the nopaline synthase (NOS) gene promoter, from *Agrobacterium tumefaciens* (U.S. Pat. No. 5,034,322 issued to Rogers et al., which is hereby incorporated by reference in its entirety), the cauliflower mosaic virus (CaMV) 35S and 19S promoters (U.S. Pat. No. 5,352,605 issued to Fraley et al., which is hereby incorporated by reference in its entirety), those derived from any of the several actin genes, which are known to be expressed in most cells types (U.S. Pat. No. 6,002,068 issued to Privalle et al., which is hereby incorporated by reference in its entirety), and the ubiquitin promoter, which is a gene product known to accumulate in many cell types.

An inducible promoter is a promoter that is capable of directly or indirectly activating transcription of one or more DNA sequences or genes in response to an inducer. In the absence of an inducer, the DNA sequences or genes will not be transcribed. The inducer can be a chemical agent, such as a metabolite, growth regulator, herbicide, or phenolic compound, or a physiological stress directly imposed upon the plant such as cold, heat, salt, toxins, or through the action of a pathogen or disease agent such as a virus or fungus. A plant cell containing an inducible promoter may be exposed to an inducer by externally applying the inducer to the cell or plant such as by spraying, watering, heating, or by exposure to the operative pathogen. An example of an appropriate inducible promoter for use in the present invention is a glucocorticoid-inducible promoter (Schena et al., "A Steroid-Inducible Gene Expression System for Plant Cells," *Proc. Natl. Acad. Sci.* 88:10421-5 (1991), which is hereby incorporated by reference in its entirety). Expression of the transgene-encoded protein is induced in the transformed plants when the transgenic plants are brought into contact with nanomolar concentrations of a glucocorticoid, or by contact with dexamethasone, a glucocorticoid analog (Schena et al., "A Steroid-Inducible Gene Expression System for Plant Cells," *Proc. Natl. Acad. Sci. USA* 88:10421-5 (1991); Aoyama et al., "A Glucocorticoid-Mediated Transcriptional Induction System in Transgenic Plants," *Plant J.* 11: 605-612 (1997), and McNellis et al., "Glucocorticoid-Inducible Expression of a Bacterial Avirulence Gene in Transgenic *Arabidopsis* Induces Hypersensitive Cell Death," *Plant J.* 14(2):247-57 (1998), which are hereby incorporated by reference in their entirety). In addition, inducible promoters include promoters that function in a tissue specific manner to regulate the gene of interest within selected tissues of the plant. Examples of such tissue specific or developmentally regulated promoters include seed, flower, fruit, or root specific promoters as are well known in the field (U.S. Pat. No. 5,750,385 issued to Shewmaker et al., which is hereby incorporated by reference in its entirety). In the preferred embodiment of the present invention, a heterologous promoter is linked to the nucleic acid of the construct, where "heterologous promoter" is defined as a promoter to which the nucleic acid of the construct is not linked in nature.

The expression system of the present invention can also include an operable 3' regulatory region, selected from among those which are capable of providing correct transcription termination and polyadenylation of mRNA for expression in the host cell of choice, operably linked to a DNA molecule which encodes for a protein of choice.

The vector of choice, promoter, and an appropriate 3' regulatory region can be ligated together to produce the DNA construct of the present invention using well known molecular cloning techniques as described in Sambrook et al., Molecular Cloning: A Laboratory Manual, Second Edition, Cold Spring Harbor Press, NY (1989), and Ausubel, F. M. et al. Current Protocols in Molecular Biology, New York, N.Y: John Wiley & Sons, (1989), which are hereby incorporated by reference in their entirety.

The efficiency of expression can be enhanced by the inclusion of appropriate transcription or translation enhancer elements (e.g., elements disclosed in Bittner et al., *Methods in Enzymol.* 153:516 (1987), which is hereby incorporated by reference in its entirety). Additionally, the gene sequence can be modified for optimal codon usage in the appropriate expression system or, alternatively, the expression host can be modified to express specific tRNA molecules to facilitate expression of the desired gene.

In addition, the recombinant expression vector can contain additional nucleotide sequences. For example, the recombinant expression vector may encode a selectable marker gene to identify host cells that have incorporated the vector. Moreover, to facilitate secretion of the protein from a host cell, the recombinant expression vector can encode a signal sequence linked to the amino-terminus of the protein, such that upon expression, the protein is synthesized with the signal sequence fused to its amino terminus. This signal sequence directs the protein into the secretory pathway of the cell and is then usually cleaved, allowing for release of the protein without the signal sequence from the host cell. Use of a signal sequence to facilitate secretion of proteins or peptides from mammalian host cells is well known in the art.

Once an expression system containing a polynucleotide according to the present invention has been prepared, it is ready to be incorporated into a host cell. Basically, this method can be carried out by transforming a host cell with the expression system of the present invention under conditions effective to yield transcription of the DNA molecule in the host cell. Recombinant molecules can be introduced into cells via transformation, particularly transduction, conjugation, mobilization, or electroporation. The DNA sequences are cloned into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable host cells include, but are not limited to, bacteria, virus, yeast, mammalian cells, insect, plant, and the like. Methods of transformation may result in transient or stable expression of the nucleic acid under control of the promoter. In one embodiment, a nucleic acid construct of the present invention is stably inserted into the genome of the recombinant plant cell as a result of the transformation, although transient expression can serve an important purpose, particularly when the plant under investigation is slow-growing.

Plant tissue suitable for transformation include leaf tissue, root tissue, meristems, zygotic and somatic embryos, callus, protoplasts, tassels, pollen, embryos, anthers, and the like. The means of transformation chosen is that most suited to the tissue to be transformed.

Transient expression in plant tissue is often achieved by particle bombardment (Klein et al., "High-Velocity Microprojectiles for Delivering Nucleic Acids Into Living Cells," *Nature* 327:70-73 (1987), which is hereby incorporated by reference in its entirety). In this method, tungsten or gold microparticles (1 to 2 μm in diameter) are coated with the DNA of interest and then bombarded at the tissue using high pressure gas. In this way, it is possible to deliver foreign DNA into the nucleus and obtain a temporal expression of the gene under the current conditions of the tissue. Biologically active particles (e.g., dried bacterial cells containing the vector and heterologous DNA) can also be propelled into plant cells. Other variations of particle bombardment, now known or hereafter developed, can also be used. An appropriate method of stably introducing the nucleic acid construct into plant cells is to infect a plant cell with *Agrobacterium tumefaciens* or *Agrobacterium rhizogenes* previously transformed with the nucleic acid construct. As described above, the Ti (or RI) plasmid of *Agrobacterium* enables the highly successful transfer of a foreign nucleic acid molecule into plant cells. Another approach to transforming plant cells with a gene which imparts resistance to pathogens is particle bombardment (also known as biolistic transformation) of the host cell, as disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports* 14:6-12 (1995), which are hereby incorporated by reference in their entirety. Yet another method of introduction is fusion of protoplasts with other entities, either minicells, cells, lysosomes, or other fusible lipid-surfaced bodies (Fraley et al., *Proc. Natl. Acad. Sci. USA* 79:1859-63 (1982), which is hereby incorporated by reference in its entirety). The nucleic acid molecule may also be introduced into the plant cells by electroporation (Fromm et al., *Proc. Natl. Acad. Sci. USA* 82:5824 (1985), which is hereby incorporated by reference in its entirety). In this technique, plant protoplasts are electroporated in the presence of plasmids containing the expression cassette. Electrical impulses of high field strength reversibly permeabilize biomembranes allowing the introduction of the plasmids. Electroporated plant protoplasts reform the cell wall, divide, and regenerate. The precise method of transformation is not critical to the practice of the present invention. Any method that results in efficient transformation of the host cell of choice is appropriate for practicing the present invention.

After transformation, the transformed plant cells must be regenerated. Plant regeneration from cultured protoplasts is described in Evans et al., *Handbook of Plant Cell Cultures*, Vol. 1: (MacMillan Publishing Co., New York, 1983); Vasil I. R. (ed.), *Cell Culture and Somatic Cell Genetics of Plants*, Acad. Press, Orlando, Vol. I, 1984, and Vol. III (1986), and Fitch et al., "Somatic Embryogenesis and Plant Regeneration from Immature Zygotic Embryos of Papaya (*Carica papaya* L.)," *Plant Cell Rep.* 9:320 (1990), which are hereby incorporated by reference in its entirety.

Means for regeneration varies from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. Efficient regeneration will depend on the medium, on the genotype, and on the history of the culture. If these three variables are controlled, then regeneration is usually reproducible and repeatable.

Preferably, transformed cells are first identified using a selection marker simultaneously introduced into the host cells along with the nucleic acid construct of the present invention. Suitable selection markers include, without limitation, markers encoding for antibiotic resistance, such as the nptII gene which confers kanamycin resistance (Fraley et al., *Proc. Natl. Acad. Sci. USA* 80:4803-4807 (1983), which is hereby incorporated by reference in its entirety), and the genes which confer resistance to gentamycin, G418, hygromycin, streptomycin, spectinomycin, tetracycline, chloramphenicol, and the like. Cells or tissues are grown on a selection medium containing the appropriate antibiotic, whereby generally only those transformants expressing the antibiotic resistance marker continue to grow. Other types of markers are also suitable for inclusion in the expression cassette of the present invention. For example, a gene encoding for herbicide tolerance, such as tolerance to sulfonylurea is useful, or the dhfr gene, which confers resistance to methotrexate (Bourouis et al., *EMBO J.* 2:1099-1104 (1983), which is hereby incorporated by reference in its entirety). Similarly, "reporter genes," which encode for enzymes providing for production of an identifiable compound are suitable. The most widely used reporter gene for gene fusion experiments has been uidA, a gene from *Escherichia coli* that encodes the β-glucuronidase protein, also known as GUS (Jefferson et al., "GUS Fusions: β Glucuronidase as a Sensitive and Versatile Gene Fusion Marker in Higher Plants," *EMBO J.* 6:3901-3907 (1987), which is hereby incorporated by reference in its entirety). Similarly, enzymes providing for production of a compound identifiable by luminescence, such as luciferase, are useful. The selection marker employed will depend on the target species; for certain target species, different antibiotics, herbicide, or biosynthesis selection markers are preferred.

Plant cells and tissues selected by means of an inhibitory agent or other selection marker are then tested for the acquisition of the viral gene by Southern blot hybridization analysis, using a probe specific to the viral genes contained in the given cassette used for transformation (Sambrook et al., "Molecular Cloning: A Laboratory Manual," Cold Spring Harbor, N.Y.: Cold Spring Harbor Press (1989), which is hereby incorporated by reference in its entirety).

After the fusion gene containing a nucleic acid construct of the present invention is stably incorporated in transgenic plants, the transgene can be transferred to other plants by sexual crossing. Any of a number of standard breeding techniques can be used, depending upon the species to be crossed. Once transgenic plants of this type are produced, the plants themselves can be cultivated in accordance with conventional procedure so that the nucleic acid construct is present in the resulting plants. Alternatively, transgenic seeds are recovered from the transgenic plants. These seeds can then be planted in the soil and cultivated using conventional procedures to produce transgenic plants.

The present invention can be utilized in conjunction with a wide variety of plants or their seeds. Suitable plants include dicots and monocots. Useful crop plants can include: alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, pear, melon, citrus, strawberry, grape, raspberry, pineapple, soybean, tobacco, tomato, sorghum, papaya, sugarcane, and coffee.

A further aspect of the present invention is directed to a method of degrading mannans and polysaccharides in plant material. This method involves providing plant material and contacting the plant material with the β-mannanase protein of the present invention under conditions effective to degrade mannans and polysaccharides in the plant material.

In a preferred embodiment, the plant material which is contacted with the β-mannanase protein of the present invention is coffee beans, although other plant materials where degradation of mannans and polysaccharides is desired may also be contacted.

It may also be desirable, pursuant to this method of the present invention, to recover soluble sugars from the degraded plant material, particularly those that result from the step of contacting the plant matter with the β-mannanase protein.

These aspects of the present invention are further illustrated by the examples below.

EXAMPLES

The following examples are provided to illustrate embodiments of the present invention, but they are by no means intended to limit its scope.

Example 1

β-Mannanase Cloning from Coffee Berry Borer (*Hypothenemus hampei*) Midgut

Sample Preparation

Coffee seeds were infected with adult insects of *Hypothenemus hampei* (Coleoptera: Scolytidae) as described in Rubio et al., "Morfologia Del Sistema Digestivo de *Hypothenemus hampei* (Ferrari)," *Cenicafe* (*Columbia*) 58:66-74 (2007), which is hereby incorporated by reference in its entirety. Briefly, infected coffee beans were dissected using a stereomicroscope and the larvae were collected in a Petri dish. Each larva was stored at 4° C. for at least 10 minutes to decrease physical activity and then placed in a glass slide with a drop of sterile distilled water and dissected under a Zeiss Estemi 2000 stereomicroscope using small forceps and 0.15 mm teasing needles. In order to isolate the midgut tissue, each larva was dissected with an incision at the prothorax and the mesothorax level, then a large incision along the larvae length to expose all the alimentary canal. Finally, after the removal of fat tissue, the midgut region was dissected and immediately deposited into a pre-chilled microcentrifuge tube with 100 μl of sterile distilled water containing 0.1% RNA Later™ reagent. All the dissected midgut tissues were stored at −80° C. until protein and RNA extraction.

Coffee Berry Borer YSST Library Construction

RNA was extracted from the midgut tissues and stored at −80° C. Polyadenylated RNA was isolated from the total RNA using Oligotex mRNA Midi Kit(Qiagen, Valencia, Calif.) according to the manufacturer's instructions. The first-strand cDNA were synthesized from mRNA using N6-NotI primer:

5'-GAGAGAGAGAGAGAGAACCGCGCGGC-CGCCNNNNNN-3' (SEQ ID NO:4)

with a cDNA Synthesis Kit (Stratagene). After second-strand synthesis, the cDNAs were prepared for unidirectional cloning by ligation with EcoRI adapters according to the manufacturer's instructions, followed by NotI digestion. The cDNAs were then fractioned on a 1% agarose gel by electrophoresis and those within an estimated size range of 300-1,000 bp excised from the gel and purified using QIAquick gel extraction kit (Qiagen, Valencia, Calif.). The fragments were ligated to an equipartite mixture of the three vectors, PYSST0, pYSST 1, and pYSST2, digested with EcoRI and NotI. Electrocompetent TOP10F' *Escherichia coli* cells (Invitro, Carsbad, Calif.) were transformed with approximately 1 μg of the resulting YSST library by electroporation (Micropulser Electroporator, Bio-Rad, Hercules, Calif.) and spread on 10-15 large LB plates. Plasmid DNA was isolated from a pooled sample of the resulting transformants using the Perfectprep Plasmid Midi kit (Eppendorf). Fifty micrograms of the YSST library was transformed into the yeast (*Saccharomyces cerevisae*) strain DBYα2445 (MATα, suc2Δ-9, lys2-801, ura3-52, ade2-101) using the YEASTMAKER Yeast Transformation System2 (BD Biosciences, San Jose, Calif.). Transformants were spread on YP sucrose plates (1% yeast extract, 2% peptone, 2% sucrose, 2% agar, pH 6.5), incubated at 30° C. for 4-9d, and visible colonies were re-streaked on sucrose plate followed by incubation at 30° C. for 2-3d. Plasmids were isolated from visible colonies as described in Hoffmann and Winston, "A Ten-Minute DNA Preparation from Yeast Efficiently Releases Autonomous Plasmids for Transformation of *Escherichia coli*," *Gene* 57:267-272 (1987), which is hereby incorporated by reference in its entirety, transformed into XL 1-blue electrocompetent *E. coli*, and purified using a Qiaprep kit (Qiagen). Plasmid inserts were sequenced using a primer corresponding to ADH1 promoter of pYSST0, pYSST1, pYSST2 (5'-TC-CTCGTCATTGTTCTCGTTCC-3') (SEQ ID NO:5) at the Bio Resource Center, Cornell University, Ithaca, N.Y. (World Wide Web.brc.cornell.edu).

RACE Amplification

An oligonucleotide primer derived from the DNA sequence corresponding to the predicted signal sequences of isolated mannanase YSST clone was used in 3'RACE with the primer as an adapter primer. To obtain the full-length cDNA sequence, 'touchdown' PCR was performed using a program with 35 cycles of 94° C. for 1 min, 63° C. for 1 min, 72° C. for 2.5 min with the annealing temperature decreasing by 1° C. every second cycle to 60° C., followed by final extension of 72° C. for 10 min. The PCR products were subcloned into the pGEM-T Easy vector (Promega, Madison, Wis.). DNA sequences were determined as describes supra. β-mannanase from *H. hampei* is an endoglycanase (endo-β-1,4-D-glucanase, EC 3.2.1.4). It is a single polypeptide chain of 320 aminoacids, with a predicted molecular mass of 35.62 kDa and the theoretical pI is 4.72, calculated from amino-acid composition.

Example 2

Heterologous Expression of β-mannanase in *Spodoptera frugiperta* (Sf9) Cells

Construction of Fusion Protein Expression Plasmid

For the construction of C-terminal Mannanase-HIS-tagged expression plasmid, the cDNAs were reamplified by PCR using a mannanase cDNA in pGEM-T Easy vector (Promega, Madison, Wis.) as a template with the following primers: 5'-CACCATGGAACCTTTTGTGGTC-3' (SEQ ID NO:6) and 5'-GACAGGGATGAAGCAGATCTGG-3' (SEQ ID NO:7). The underlined portion of SEQ ID NO:6 was introduced for directional TOPO cloning. The latter reverse primer lacks the stop codon in the native β-mannanase cDNA. The resulting cDNA was cloned into pENTR/β-TOPO vector (Invitrogen, Carlsbad, Calif.) and designated pENTR/β-Mann.

DNA Baculovirus Recombination and Transfection

Baculovirus construction and protein expression in Sf9 cells were performed according to the BaculoDirect Baculovirus Expression System protocol from Invitrogen (Carlsbad, Calif.). *Spodoptera frugiperda* Sf9 cells were transfected with recombinant bacmid DNA for production of the baculovirus particles. Cells were cultured at 27° C. in SF900-II medium (Life Technologies) supplemented with 100 U/ml penicillin and 100 µg/ml streptomycin. For transfection, $9 \times 10^5$ cells were plated in 35-mm tissue culture flasks and incubated for 1 h in 2 ml Sf900-II SFM (Life Technologies) without antibiotics to allow adhesion of the cells to the dish. The medium was then changed to 1 ml serum-free Sf900-II without antibiotics, containing recombinant bacmid DNA (5 µl of a standard mini-preparation of plasmid DNA) that had been pre-incubated for 30 min at room temperature with CellFectin (6 µl) (Life Technologies). Cells were incubated with the liposome-DNA complex at 27° C. for 5 h. The transfection medium was removed and 2 ml of SF900-II medium, containing antibiotics, was added. PENT™/Man plasmid was transfected into Sf9 cells and nonrecombinant bacmid (Bd) DNA and PENT™/CAT were used as, respectively, negative and positive controls. Transfected cells were incubated at 27° C. for 72 h allowing baculovirus production and release into the culture medium. The culture medium from each transfection was collected, clarified (500 g for 5 min), and stored at 4° C. as a master virus stock. Transfection efficiency, recombinant baculovirus (Bv-Man) and nonrecombinant baculovirus (Bv) production were monitored by visualization of the cytopathic effect displayed by transfected cells within 48 h after subculturing under a phase contrast microscope and assaying the presence of baculovirus DNA through PCR analysis. To this end, baculovirus present in 50 µl of infected culture supernatant was sedimented at 12 000 g for 10 min in a microcentrifuge tube, and a volume (25 µl) of proteinase K buffer (10 mM Tris-HCl, pH 7.8; 5 mM EDTA; 0.5% SDS) containing 50 µg/ml of proteinase K (Sambrook et al., 1989) was added to the pellet to digest viral proteins for 1 h at 56° C. An additional heating at 95° C. for 20 min was included in order to inactivate the enzyme before proceeding to the PCR step. Viral DNA amplification was carried out using 2 µl of this DNA preparation as the template at the same conditions and primers described above. The cells were selected with ganciclovir for 120 hours, and the resulting viral stock was amplified twice by infecting the Sf9 cells.

Amplification of Baculovirus Stocks

For amplification of the baculovirus master stocks, $1 \times 10^6$ Sf9 cells were plated in a 25-cm² flask and incubated for 1 h with 10 µl of baculovirus master stock in 1 ml of SF900-II medium containing antibiotics (corresponding to an MOI of 0.01-0.1). After this period, the medium was completed to 4.5 ml and the infected cells were incubated for 48 h at 27° C. The culture medium was collected, clarified (500 g for 5 min), and stored at 4° C. as viral stocks for recombinant protein production.

Scale Up Production of Recombinant β-Mannanase

Cells of *S. frugiperta* were plated in a 225 cm² with 50 ml of culture medium and incubated as above. Cells were transfected at log phase using 500 µL of a viral stock P3 (titer $3.44 \times 10^6$ pfu/ml). After 96 hours, the culture medium was collected, clarified (500 g for 5 min), and the recombinant β-mannanase was purified using the MagneHis System® (Promega, Madison, Wis.). This resulted in the production of 2.4 mg of purified β-mannanase per 100 ml of culture.

Example 3

Purification of Recombinant β-Mannanase

Figure 2:
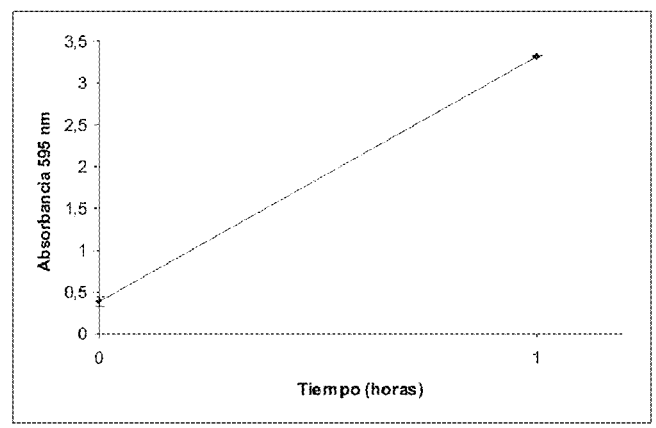
FIG. 2 is a graph showing time course of AZC-galactomannan hydrolysis with soluble recombinant β-mannanase from *H. hampei*. Enzymatic activity was determined by blue color increase of absorbance across time. β-mannanase activity is mean±SE for three reactions.

MagneHis Ni-Particles® (Promega, Madison, Wis.) pull-down assays were performed according to the manufacturer's protocol. Briefly, 10 ml of culture medium after removing cells was mixed with 300 µl of MagneHis Ni-Particles® and incubated at room temperature for 2 min with gentle shaking. After incubation, the tube was placed in a magnetic stand for 30 seconds to allow the MagneHis Ni-Particles® to be captured by the magnet, and the supernatant was removed. The MagneHis Ni-Particles® were washed three times with the binding/wash buffer. Pure β-mannanase-6xHis-tagged protein was subjected to SDS/PAGE (FIG. 1) and functional assay (FIG. 2).

Example 4

Determination of Enzyme Activity Using β-Galactomannans from Carob Tree Seeds

Azurine-crosslinked-Galactomannan was prepared by dyeing and crosslinking galactomannan polysaccharide extracted from carob seed flour (AZCL-galactomannan®; Megazyme International Ireland Ltd.). The Carob tree, *Ceratonia siliqua*, is an evergreen shrub or tree, native to the Mediterranean region, cultivated for its edible seed pods. This substrate is insoluble in buffered solutions, but rapidly hydrates to form gel particles which are readily and rapidly hydrolysed by specific endo-hydrolases releasing soluble dye-labeled fragments according to Marraccini et al., "Molecular and Biochemical Characterization of ENDO-β-MANNANASEs from Germinating Coffee (*Coffea arabica*) Grains," *Planta* 213:296-308 (2001), which is hereby incorporated by reference in its entirety. An aliquot of 20 µL of the recombinant β-mannanase-6xHis-tagged protein mixed in substrate solution [1% (w/v) AZCL-galactomannan® in 0.2 M acetate buffer (pH 5.0)] was incubated at 37° C. with gentle shaking. Aliquots of 200 µL were removed every 30 min and heated at 100° C. for 5 min to stop the reaction. Each aliquot was centrifuged at 13k rpm for 5 min and the absorbance was measured at $\lambda_{595}$ nm (FIG. 2).

Example 5

Determination of Enzyme Activity Using β-Galactomannan from Coffee Beans

Coffee β-Galactomannan Purification

A sequential fractionation procedure based on a delignification treatment, an acid wash, and subsequent alkali extraction (as in Bradbury et al., "Chemical Structures of Green Coffee Bean Polysaccharides," *J. Agric. Food Chem.* 38:389-

392 (1990), which is hereby incorporated by reference in its entirety) was used to isolate pure β-mannan from green coffee beans. Ground green *Coffea arabica* coffee beans were Soxhlet-extracted with chloroform/methanol (2:1) and petroleum ether (5h) to remove lipids and with aqueous ethanol (95%, overnight) to remove low molecular weight carbohydrate. Defatted beans were hot water extracted and then delignified with weakly acidic sodium chloride solution, according to the method of Wolfrom and Patin, "Carbohydrates of the Coffee Bean. IV. An Arabinogalactan," *J. Org. Chem.* 30:4060-4063 (1965), which is hereby incorporated by reference in its entirety, to give a white holocellulose product. Most of the arabinogalactan polymer was solubilized, in a partially hydrolyzed form, by washing with dilute hydrochloric acid (1%, 80° C.). The mannan was then isolated in discrete fractions by extraction (overnight, 4° C.) with 2.5 and 10% sodium hydroxide solutions. Addition of ethanol to the 2.5% NaOH extracts led to a precipitate containing arabinogalactan and mannan. Neutralization of the 10% NaOH extracts led to rapid formation of a white precipitate, which was removed by filtration after the mixture was allowed to stand overnight at 4° C. A further fraction was obtained by addition of ethanol to the filtrate. The precipitates were all washed with ethanol and diethyl ether before drying. The mannan substrate used in this work was the fraction precipitated by neutralization of the 10% NaOH extracts, which contained 94% mannan by weight.

Effect of pH and Temperature on the Activity of the Recombinant β-Mannanase from *H. hampei*

Figure 3:
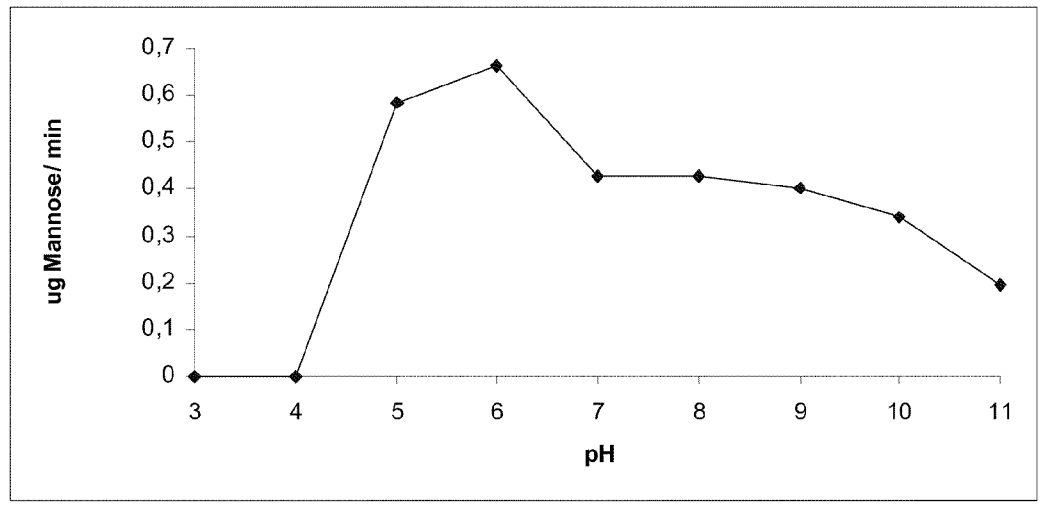
FIG. 3 is a graph showing the effect of pH on the activity of recombinant β-mannanase from *H. hampei*, according to the present invention. The buffer was 200 mM sodium acetate pH 3.0, 4.0, 5.0, 6.0, 7.0, 8.0, 9.0, 10.0, and 11.0.
Figure 4:
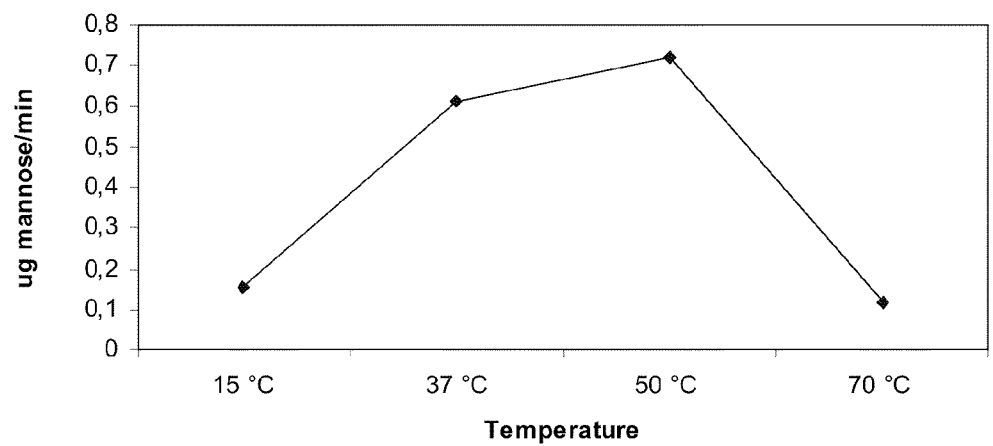
FIG. 4 is a graph showing the effect of temperature on the activity of the recombinant β-mannanase from *H. hampei*. Enzyme solutions in 200 mM sodium acetate buffer pH 5.0 were incubated at various temperatures for 120 minutes and the activities were measured as described in the Examples (infra).

In order to test enzyme activity against coffee galactomannans, the β-mannanase activity was determined by the dinitrosalicylic acid assay of Bernfeld, P. In: Collowick S. P. and Kaplan N. O. (eds.), *Methods in Enzymology*, Vol. I, Academic Press, New York, pp. 149-158 (1955), which is hereby incorporated by reference in its entirety. The optimal pH of the enzyme activity against coffee galactomannan was determined at different pH values ranging from 4.0 to 11. The buffer was 200 mM sodium-acetate and 100 mM Sodium chloride at 37° C. The highest enzyme activity was observed at pH 6.0 (FIG. 3). The effect of temperature on activity of the recombinant β-mannanase against coffee galactomannan was examined in the temperature range of 15° C. to 70° C. using the same bufffer at pH 6.0 (FIG. 4). The enzyme showed maximum activity around 50° C. The activity of the enzyme decreased sharply with further increases in temperature.

Although the invention has been described in detail for the purpose of illustration, it is understood that such detail is solely for that purpose, and variations can be made therein by those skilled in the art without departing from the spirit and scope of the invention which is defined by the following claims.

What is claimed is:

1. An isolated polynucleotide encoding a β-mannanase protein having an amino acid sequence which is at least 95% similar to the amino acid sequence of SEQ ID NO: 1.

2. The isolated polynucleotide of claim 1, wherein the polynucleotide encodes a protein having the amino acid sequence of SEQ ID NO: 1.

3. The isolated polynucleotide of claim 1, wherein the polynucleotide has the nucleotide sequence of SEQ ID NO: 2.

4. An isolated expression system containing the polynucleotide of claim 1.

5. An isolated host cell containing the polynucleotide of claim 1.

6. The host cell of claim 5, wherein the host cell is a bacterial cell.

7. A method of recombinantly producing β-mannanase protein, said method comprising:
providing the host cell of claim 5;
culturing the host cell under conditions effective for the host cell to express β-mannanase protein; and
recovering the β-mannanase protein.

8. The host cell of claim 5, wherein the host cell is a eukaryotic cell.

9. The host cell of claim 8, wherein the eukaryotic cell is selected from the group consisting of plant cells, fungal cells and insect cells.

* * * * *

SEQUENCE LISTING

```
<160> NUMBER OF SEQ ID NOS: 7

<210> SEQ ID NO 1
<211> LENGTH: 321
<212> TYPE: PRT
<213> ORGANISM: Hypothenemus hampei

<400> SEQUENCE: 1

Met Thr Ala Asp Thr Leu Thr Arg Ala Leu Leu Leu Leu Leu Leu Leu
1               5                   10                  15

Arg Ala Ala Ala Ala Val Pro Gly Phe Thr Val Ser Gly Thr Arg Ile
            20                  25                  30

Leu Asp Ala Asn Gly Gln Glu Phe Met Ile Arg Gly Val Ser His Ala
        35                  40                  45

His Thr Trp Tyr Lys Asp Asp Ile Asn Gly Ala Ile Thr Ser Ile Ala
    50                  55                  60

Ala Ala Gly Ala Asn Thr Val Arg Ile Val Leu Ser Asn Gly Gly Gln
65                  70                  75                  80

Trp Thr Lys Asp Asn Leu Asp Ser Val Gln Asn Ile Leu Ser Leu Cys
                85                  90                  95

Glu Ser His Lys Leu Ile Ala Met Leu Glu Val His Asp Ala Thr Gly
            100                 105                 110

Asn Asp Ser Gln Glu Thr Leu Glu Asn Ala Val Asn Tyr Trp Lys Glu
        115                 120                 125

Leu Arg Asp Leu Leu Ile Gly Lys Glu Asp Arg Val Ile Ile Asn Ile
    130                 135                 140

Ala Asn Glu Trp Phe Gly Thr Trp Asp Thr Ala Gly Trp Ala Asp Gly
145                 150                 155                 160

Tyr Lys Val Val Ile Pro Glu Leu Arg Asn Ala Gly Leu Glu His Leu
                165                 170                 175
```

```
Leu Val Val Asp Thr Ala Gly Tyr Gly Gln Tyr Pro Gln Ala Ile Phe
            180                 185                 190

Glu Lys Gly Lys Glu Val Phe Gln Thr Asp Leu Leu Ala Arg Thr Val
        195                 200                 205

Phe Ser Ile His Met Tyr Glu Tyr Ala Ala Thr Asp Val Thr Met Ile
    210                 215                 220

Lys Gly Asn Ile Asp Ser Ala Leu Asn Thr Gly Ile Pro Val Ile Ile
225                 230                 235                 240

Gly Glu Phe Gly Asp Arg Lys Pro Glu Ser Gln His Val Asp Ile Asp
                245                 250                 255

Thr Ile Met Ser Tyr Thr Arg Glu Lys Ser Val Gly Trp Leu Ala Trp
            260                 265                 270

Ser Trp Tyr Gly Asn Gly Asn Asp Glu Ser Ile Leu Asp Leu Thr Asn
        275                 280                 285

Gly Pro Ser Gly Asp Tyr Ser Leu Thr Asn Val Gly Ser Gln Ile Val
    290                 295                 300

Asp Ser Glu Asn Gly Ile Arg Lys Thr Ser Thr Ile Cys Ser Ile Phe
305                 310                 315                 320

Asn
```

<210> SEQ ID NO 2
<211> LENGTH: 1063
<212> TYPE: DNA
<213> ORGANISM: Hypothenemus hampei

<400> SEQUENCE: 2

```
gctgatcggg tgtgtactca attctttaag gagtttacaa tatgaccgct gatacattaa      60
cgcgggcact gctgctgttg ctgttgttgc gcgctgctgc tgctgtaccc ggattcacgg     120
tttccggtac tcgaatttta gatgctaacg gtcaggaatt tatgataaga ggggtcagtc     180
acgcacatac ctggtataag gatgatatta atggggccat cacatccatc gctgctgctg     240
gcgccaacac ggttcgcatt gtactttcta atggcggaca gtggacaaaa gacaacctgg     300
attcagttca gaacattctg tccctctgtg agagccataa gcttattgcc atgctggaag     360
ttcacgatgc caccggcaat gacagccaag aaacactgga aaatgccgtg aattactgga     420
aagagcttcg ggacttgctc attggtaagg aagacagagt tattatcaat atagccaatg     480
agtggttcgg tacctgggat actgctggct gggccgacgg ttataaagtt gtcattccgg     540
aactacgtaa cgccggactg aacacctgc tggttgtaga cacagcggga tacgacaat      600
atcctcaagc tattttgaa aaaggtaagg aggttttcca gacagacctt cttgcccgca     660
cggtgttttc cattcacatg tatgaatatg cagcgacgga tgtaacaatg ataaaaggaa     720
atattgactc ggccttgaat acaggcatcc cggtgattat tggagaattt ggtgaccgaa     780
aaccggagtc gcagcatgtt gatatcgata ccatcatgag ctacactcgc gagaaatccg     840
taggctggtt ggcctggtcc tggtacggta acggtaacga tgaatcaatt cttgacctga     900
cgaacggacc tagcggagat tacagtctta ctaacgtggg gagtcaaatt gttgacagtg     960
agaacggcat tcgcaaaacc tccacaatct gttcaatatt caattaaaaa aaaagatgtt    1020
tgtttgtgca ttttttgttat aataaacgtt tcatttgcat att                      1063
```

<210> SEQ ID NO 3
<211> LENGTH: 10274
<212> TYPE: DNA
<213> ORGANISM: Hypothenemus hampei

```
<400> SEQUENCE: 3
atggttgagt tcaccaatca agaatatgca gacatgcatt tgatttatgg ccaagccaat      60
ggcaattcct acgaagcgcg cagactctac gcacgtagat atcctaatcg agactacct      120
gatccaaaaa catttccaaa tattcacatt cgactatgtg aaactggaac atataaacag     180
ttcagtggtt tcgaaggagt acatcaaatc gcgagaactc cagaaatcga agaagccgtt     240
ctaaatagtg ttgaagccga tcctgctacg agcacaagga aaattgcaat aacattgaac     300
atttcattta tgcttgtctg aagaattctg actgataacc ttttgtatcc ttaccacctt     360
acaagggttc aagctcttct cccacgagac tttcctttag gcgtaaattt ttgcgagtag     420
ttcttacaaa tgctggctca aaatccgtcg tttgcatcgt ttgcgtcgtt ttgtttattt     480
tatttacgga tgaagcaaat ttttcaagaa attccatccg aaattttcat aatgaacatt     540
tttggggaga agaaaatcca catttagtac gagaaaacaa ttttcaacat caattttctg     600
tcaacgtttg gcaggaatt attggcgatt atttaatagg accatttttt ctgtcgaaga      660
ggttgaatgg tggctattat catcggtttt tcgaagagga acttcccgta cttttagatg     720
aggtaccgct tcttttgaga aaccaaatgt ggctaatgca cgatggtgcg ccagtccatt     780
ttagtcggga agtaagggag ttcctaaatg aacattatca caaccgttgg attgatcgag     840
ggggaactca gtcatggccc ccgaggtccc cggacctgaa tagtctggat ttttttttct     900
agggacatct caaatccttg gtgtaccaaa ccccaattaa cacagtggag gaattgcgaa     960
acagaatagt cgattcatgt aacgtcattc gcaatactcc tggtattttt gaaagagtcc    1020
gccggtctat gaggcacaga gcggaatctt gcatcttagc aagaggagga cattttcaac    1080
agttcctata gtcttgtttt atttagatta aattacttt actgttacct tacgaattta    1140
atacataaga ttcattgtac tcttttgttg tacgttttcc ttaatatgca tcggtaactg    1200
tttatgcaaa ttttttcgcaa atgataaaag atacgagaaa aatgcaagag atcaaaaagt    1260
aagagaaata gacaaggaat ctaaatgtga aatcaaaatt tatacatagt gttccaaaaa    1320
aaagttagga agcaaaaaat agcacatgac ccaagaaaac ataagaccct gtatatggag    1380
agcaacgatt ttgccatttt catatagagg ctcttaaaaa atatagatat accaaatttc    1440
attaaattat ctttaggcat aagaaagaaa atagtagaaa atttaaaaaa aatcaaactt    1500
tatcaccctg tatatcaaaa atggtgcgtt tttccccata ggtgtattag cattttttc    1560
ttattttgcc gaatactatc accccctgaa atatctccat gatgatctgt tacaccctgt    1620
acacctaaaa agtaaaataa taaaacgttt aaattttatc ttttaacgta gataagattt    1680
tgcgtccttt gtttccttct aagttttaat cgagatttcg cctcattttc gctcattcgc    1740
cagaagacct cagtgaaagc gattcattaa gtctgaaatt taactttgtt ccctaccgaa    1800
tattctttt ctgacgatag acgatagctg atcgggtgtg tactcaattc tttaaggagt    1860
ttacaatatg accgctgata cattaacgcg ggcactgctg ctgttgctgt tgttgcgcgc    1920
tgctgctgct gtacccggat tcacggtttc cggtactcga atttagatg ctaacggtca    1980
ggaatttatg ataagagggg tcagtcacgc acatacctgg tataaggatg atattaatgg    2040
ggccatcaca tccatcgctg ctgctggcgc caacacggtt cgcattgtac tttctaatgg    2100
cggacagtgg acaaaagaca acctggattc agttcagaac attctgtccc tctgtgagag    2160
ccataagctt attgccatgc tggaagttca cgatgccacc ggcaatgaca gccaagaaac    2220
actggaaaat gccgtgaatt actggaaaga gcttcgggac ttgctcattg gtaaggaaga    2280
cagagttatt atcaatatag ccaatgagtg gttcggtacc tgggatactg ctggctgggc    2340
```

```
cgacggttat aaagttgtca ttccggaact acgtaacgcc ggactggaac acctgctggt    2400
tgtagacaca gcgggatacg gacaatatcc tcaagctatt tttgaaaaag gtaaggaggt    2460
tttccagaca gaccttcttg cccgcacggt gttttccatt cacatgtatg aatatgcagc    2520
gacggatgta acaatgataa aaggaaatat tgactcggcc ttgaatacag gcatcccggt    2580
gattattgga gaatttggtg accgaaaacc ggagtcgcag catgttgata tcgataccat    2640
catgagctac actcgcgaga atccgtagg ctggttggcc tggtcctggt acggtaacgg    2700
taacgatgaa tcaattcttg acctgacgaa cggacctagc ggagattaca gtcttactaa    2760
cgtggggagt caaattgttg acagtgagaa cggcattcgc aaaacctcca caatctgttc    2820
aatattcaat taaaaaaaaa gatgtttgtt tgtgcattt tgttataata acgtttcat    2880 ttgcatatta aatatactaa tccaatatat atttatagac aatagattat taaaaaagta    2940
aattttaaaa taacttcttc aaaaaagaac atttacgctc aaagtgacct atagacgtca    3000
ataatttaaa atgtcactct tcgcacattg acaataacct gcatagacgt ctatgaacgt    3060
cgttgtctat agacgtgttc ctttaattgt tttctaaagc tttgatcaat tggttcagaa    3120
aaacggttca atagattcat ttaataattt acaggactat tggggtaca ttaggctata    3180 aaacggcctc tcaatatttg tcttcccatc aatatttaaa aagtaatagt agatttgtta    3240
aaggactgta aaatgtaatt ttttagtagt ttttccaaat taaagctaag agtaaaaaaa    3300 acggttttc tacaaaagtc atggaagggt tttgtaggga atttaatcag gttttttaaaa    3360 ctatccttga aattaaagtt tacttaagcg atcactggtt gctgagatat cgatgatcaa    3420
agataaaagg atcctttttc tttcaaagtt agatgtctca gcaagggatt gacgtagatg    3480
tatgaaaaaa aaacaaaat gaagctgaat aaacaaggta accgaccact gtacgacaag    3540
ggttcaaatg gaaaaaatt tctgagaccc atggagactt tagaagaaga agaaaatttt    3600
gaaaaatgtt tacctcgcgc catttcttgg gattgcgcgg taaccataac tccaaggaa    3660 attccgatgt aagatctgaa aactataaaa cattaagctt caaaatgctt tttctccaa    3720 ctcgatacga ccgttttttc acaaagatac tcaaagaaca ctaaaaaaaa taaaaaaagg    3780
tttttacttt aattttttgg attagtatta ttaacattat ttaatctaaa ataatactga    3840
tattggtatt aacttccacc aggtacactg gtttcaatag aaacgttacc aatttagtta    3900
catagcatca aagaaaagaa tgacattatg atcatcaatt ataattgatt gttcgattat    3960
aatataacta ttattgatta ttatattatt ataattctct taggtattaa gcccttaagt    4020
caaaaatcgt agttttctac aaaacgagat taaaaatttt ataacgctat gcaacagaaa    4080
aaaaaattca ctgggtttac agtacgtggt gatgatacct cactatttac tcaattaata    4140
tttatatata aaatagtccc atcaattatt taaattttca aaaaaaaat ttattaaatt    4200 gttcaacaaa gagttaacaa taatttcaca atagttaaga actatttct taattttcaa    4260 tatggccccc ttcctgtaaa atacacttat ctattcgttt tctgatgtgt tgcacaactt    4320
aaataataaa tgttgtaata tttcttgaaa atttaattaa ggttaccaga tgtcacttt    4380 ttacaattat tctaacaaga gttgagtgat agtttagggt tcgatccctg ctacctccga    4440
tatttttttt tttcgttttt ttttgttaa taacaatagt aataattgtc aaaataatta    4500
aaaacgataa aaataattta tttgacgcat tttacagtta tttaaagctt gtaatgagag    4560
aatttatatg attcgcatat taaattaagg atttcacta caaatttcat atttcaaaaa    4620
caattggtcc tattttaata aaattatcta ccaggaggtt tttgatgatg ctctttcata    4680
atatgttaaa aaaatgcgtt taaaattacc ctaatacatt tttctgtaaa atctaccta    4740
```

-continued

```
atatttaact ataaaaacgt acgccaatga cgaagggaaa ccatttttagg caaatcacaa    4800 tcggaattca aagatacaca actgatccaa atttgaagtg aatcggctaa acagttttg     4860 agatacaaaa gtggctccat gaatcgtgcg acatactata tgcgatcaaa ataagacttt    4920
tttttcctat aaacatgtgc cctaaaatgc accccctcca aactacagcc attctaagtt    4980
gcgcgacaaa aatcaattat tttaaatttt gactacagtt atggatcaaa ttttttgaaaa   5040 attgcacatc cgttttttctt aaacactgta ttcattctt gctttaaaaa taacgtaacc    5100
ctaattttag agaagatgga gagggatcca cttattgcgt aaataaaatt taatgttttcc   5160 aacgagaaat cctaacttta accatcagca tctagtagac catggaaaaa tctaaaattt    5220
atctctagca ttttcttaat gcaactaatc gaatctttac aggacctgac ataaaaaaat    5280
taattgatga tacctctttt ttatcaagtc tcatttacat agaataacag gcatgattag    5340
catttgttga cgtcacaaaa aattttctcg gcaattacaa atcaacagat ttctgtgaaa    5400
aaattaattt aatgttgaat gcctatcaga aattagggtg caatatatca ctgaaaattc    5460
atttcttgca atatcactta agttttttcc gaaaaatatg gattcagtta gtaatgaact    5520
aggtatatgt gcggtaaatt tatgttgcaa aaaaatgtac gcagattacc tgaattataa    5580
caacaaagtt gtcgaaaaat gtcgaaacac ctccgaaaat tgaaacatag caaaaattat    5640
ccgagtcatt tatgcacttg aattcgtgat ttcttttact catttcacaa atttattaca    5700
tgattaaaat taaattattt attaaattac aagagaatga taaaaaaaat aattaaggct    5760
tttaaatgtt gtatatgaac tgtcacaccg taacagattt gtcaacatat taacaattga    5820
cagtaaaaat ttcaaattta taattcggtc atccattaga aaattcataa cttcactatt    5880
tatccataaa tttgcatcca aagtaacttg ttctttttcat gaatgtgtca gctctacata   5940
aaacaattga aactggacct atctttgcga tttctatttt ttccagggcc atatgggaaa   6000
ctttgcaata aatcttgtgc aataaattat gacaattagg aatatttggt gcggtgtaca    6060
tattatatac aggttgaaga aaatacctcc cccataaaag ggccttcaaa atagtctaat    6120 acaatttgc ccttaaacga acagggaaga taatattaaa ggatattgaa atttatatgg    6180
gttttcctat tgtcggtccg gagggcaac atccaatata ctatatgaaa taagttgtc    6240 tatagttagt acattgttaa taatttgatt ttcatatatt ctgtattcag ttttctaccgt   6300 acaagtagcg gcggagatgt ggatgtcatg tattattaaa cttgtatgga aaaaaaggat    6360
aaaaaaggac acttatatct ccaccattga tgaatggtta aagctggtaa ttttttggaa    6420
tacacctacc gatatgctaa actcatatac gaaatttggt taaaaaatct taagccgttt    6480
tggaatttaa aaaataaaga aatgttcttt tttttaaact ttaacaccct gtatctcgga   6540
aacggtgcgt ttgcgggccc atgttcatat aaactttttt gcttattttt gtctgaagaa    6600
tcatcccttg aaatttatgc acgtacttaa ttaacaccct gtatttcacg taccatgtcc    6660
tactatacct aaactcaaca gttggcgaga aattttgttg tcgtacctgg ttttttgggcc   6720 atcctgtata catggattta tcatcacaaa aacctcaacc aaaaataaaa attgacgtgt    6780
atgagcgttt tttttttttg aaaaacaaat ttctgaattt taaatgaatg tattccttat    6840
tttatcataa acctgtatat aaatttaaaa aaaacgtgat gtgatacgtg aaaactaagt    6900
tgttatttgg attcagcagg acaaaattta tatgttttat ctaaaattat gcaaaaaata    6960
ttttcatcgc agaccgtgt tatcaatgta aaaattaatt aaaccccctc gtaaaagcca    7020 gcgtttgac atttgaatgt ttccgcccca atgttgaagg gaaaaataaa aagttactag    7080
aatgtaacta gttaggctgc catatttgga gtaacatgtt ccctctctct ctctaacaca    7140
```

```
cgtgaacata actttgcggt actgtataga tttagtgact gtacctacat agtcatacgt    7200
atggaaactt atacagtgta tcaatttaaa aactagcaat ggagaatatc ttctaaatga    7260
aaagtgctat caggacgatc tcaaaaacgt atcgggggat tcgaaaagga accaaaatga    7320
tatattaatc aatccgtttt cacttatccc ctcgccccca accaccccaa cgttcagaat    7380
ttcaaatggc accatctgtc atgtaatacc tcaaatggaa ggtatttcaa aactgcattt    7440
aggggtataa ttagatttta atttattgat tcgttttga gaaaaagtgc ctcaaaaagg    7500
taaaattaaa aattttaata ttgtttctta caaaaacaat taggttttca atacatgttg    7560
ttaggaacag ggccggattt agggcagggc aggcggggct actgcccgg ggcctccaca    7620
aggaaggggc ccccacaata gagaaaaata aatatcgaaa tttcgacggg tcagcaactt    7680
ttaattttt ttagtttttt caatacttaa gtgtctttcg ggacccgtgg agcgaattgg    7740
ggtgctgggt ggggtaaaca actagctccg agtgtgctaa ttgcggcgtt ctttaaaaaa    7800
aataatttat ttttgtttct ttttttcatt ttctggcgtt tcctggatgc caaaaatatg    7860
tttttttct caaaactgta aatgtcgtta aagcgttacg daccccaagt ttccatttac    7920
tgtcaatttt ttatttatc aagcatctcg gtggcaatac tttttttttta atgtgtaatt    7980
tgtaatttgt gctcatgagt taaaaagaaa taaaataagt aaaaagaaat tccaaggttt    8040
tataaaaagt atatatggta accgggtgac tattaaaatt tcttctcaag taggctttgg    8100
aattatttga caccgagtcc gtatgtctta gatttattaa cagattcgta tttaagtgag    8160
gttgggttta tttgtttata ttcgaaacta agtaaagaac atatcaaaga cttacggact    8220
cgctgtcaaa taattccaca gcctacttga gaagaaattt taatagtcac ccgttataaa    8280
tacgatttaa atcttacggt tggcaacact gtcgtggtta agaagtgtcc gagtgtagcg    8340
tgctcgaagc ggggaatccc taaattttat tagaagctac ggacgtattg caacaaaagt    8400
aaaatcttct gaattatat ctacaaacac acgtaagtat tttcgtattt atcttgtgat    8460
ctataagata taatgaattt tatatttcat tgtgcaatta cgaaaatttg ttttttttc    8520
ttaaaggagc gatatgcttt aaagagcaaa aacgtaaaca gaggttatgg aggttttatt    8580
ccacgactac attcttattt tcttaagatt tcttttacaa tggtattatg agtgatcgcc    8640
ataaaactcc tcgagttttc gctagtggat cccaaaaaag gaaattgcaa acagaacgtg    8700
aaaaaaaaaa agtgaagaaa atttagctaa aatacccaaa ttgaccaact attttacatc    8760
gacacccaaa caaaaacttc cgcaagatcc tgaaaaatca gcagaagatt cagcagtaga    8820
tggagatggg gttgatagta atcaagataa tccagctgtt acatcaggcg acaccatagg    8880
atcttcaaaa acttgtagtc acaatcaaga ggaagtagat tttcgtggtt tcaaaaatga    8940
cattggtctt tggcctgacg tcataacaga agaaatgatc aaatattggg cgaagaaggg    9000
ttccacaaaa ctgcaaaact gtgatgaagt ttctctgcag aattcagttc tccaagacca    9060
gtcgcaagat aataaaaact ttgttcggaa atgttcaaag aatatgttta cacgtcgcaa    9120
tcaaaatcaa gagactgtta atcgattctg gctttgtttt tctccaacta agggaaaagt    9180
atattgctat gcatgtaaat taatgtccac tcaaaaacga agctaagtgg ggaaggcttc    9240
agtgactgga aacatgcatc tgagcggctg tacgagcatg agatttcaaa aactcatttg    9300
gaatcagtga tgaatttagt gcaacgagga gaagtcacag gacgtatcga tcaagagtta    9360
acgatacaag aggcacaaca aattgaatat tggcgaaaaa ttcttacaat tgtcgtcagt    9420
acgattaaat tcattgctga acgcggatta gcctttcgag gagacgatga aattattgga    9480
tcatcgagaa atggcaattt tctgggtatt ttagaattgc tagccgagta cgaaccaatc    9540
```

```
ttggcagctc atttaaaaca gcatgcaaac aaagggagag gtcacgtcaa ttatctttct    9600
tctacgatct gcgaagaact gacaaattcc atgggtgatc aagtgttcaa tgaaatcgta    9660
gcaaggatta aaaatcaaa  gtactattct gtttcagtgg actctactcc tgacgaatct    9720
catatcgatc aacttactat agttattcgc tatattgaag gatcgatgcc aaaggaacga    9780
tttcttattt tttaccaaat tgcggtcata ctggtgaagc cacagcaaaa gctttactac    9840
aatttttaag ttaccatcaa attgacatcc ttaattgccg aggtcaatcg tacgacaatg    9900
ctgcaaatat gagtggtaaa tatcaaggga tgcaagctct tattttgcag aaaaatcatt    9960
tatctacgtt tgtaccatgt tgtggtcact cactcaactt agttggaaag gcagctgcta   10020
actcttgtgc atcggcagtt caattctttg atttcgttca gaatttatat acgtttttta   10080
cagcaagtac acaacgatac cgaattctgt ctgaaaaatt atcagagaaa aaagcggac    10140 agtcatatgt tttaaaaaat cttagcgata ctcgctggtc atgtagggtt gcagccacga   10200
aggccattgt tatgggatat tctgaaatcg aagaagctct aaccagcata tcttctgata   10260
aggaacagaa agat                                                     10274

<210> SEQ ID NO 4
<211> LENGTH: 36
<212> TYPE: DNA
<213> ORGANISM: Artificial
<220> FEATURE:
<223> OTHER INFORMATION: N6-NotI primer
<220> FEATURE:
<221> NAME/KEY: misc_feature
<222> LOCATION: (31)..(36)
<223> OTHER INFORMATION: n is a, c, g, or t

<400> SEQUENCE: 4
gagagagaga gagagaaccg cgcggccgcc nnnnnn                                36

<210> SEQ ID NO 5
<211> LENGTH: 22
<212> TYPE: DNA
<213> ORGANISM: Artificial
<220> FEATURE:
<223> OTHER INFORMATION: primer corresponding to ADH1 promoter of
      pYSST0, pYSST1, pYSST2

<400> SEQUENCE: 5
tcctcgtcat tgttctcgtt cc                                               22

<210> SEQ ID NO 6
<211> LENGTH: 22
<212> TYPE: DNA
<213> ORGANISM: Artificial
<220> FEATURE:
<223> OTHER INFORMATION: primer sequence

<400> SEQUENCE: 6
caccatggaa ccttttgtgg tc                                               22

<210> SEQ ID NO 7
<211> LENGTH: 22
<212> TYPE: DNA
<213> ORGANISM: Artificial
<220> FEATURE:
<223> OTHER INFORMATION: primer sequence

<400> SEQUENCE: 7
gacagggatg aagcagatct gg                                               22
```